(12) United States Patent
Lindegger et al.

(10) Patent No.: US 8,373,421 B2
(45) Date of Patent: Feb. 12, 2013

(54) AMBULATORY INFUSION DEVICE WITH SENSOR TESTING UNIT

(75) Inventors: Stefan Lindegger, Huttwil (CH); Reto Schrotberger, Bern (CH); Alex Muri, Liebefeld (CH)

(73) Assignee: Roche Diagnostics International AG, Rotkreuz (CH)

( * ) Notice: Subject to any disclaimer, the term of this patent is extended or adjusted under 35 U.S.C. 154(b) by 501 days.

(21) Appl. No.: 12/761,445

(22) Filed: Apr. 16, 2010

(65) Prior Publication Data
US 2010/0264931 A1 Oct. 21, 2010

(30) Foreign Application Priority Data
Apr. 16, 2009 (EP) .................................. 09005407

(51) Int. Cl.
*G01R 31/14* (2006.01)
*G01R 31/28* (2006.01)
(52) U.S. Cl. ........ 324/511; 324/522; 324/531; 324/532; 324/549; 73/1.16; 73/1.57; 73/709; 73/714; 73/753; 604/65; 604/66; 604/67
(58) Field of Classification Search .................. 324/511, 324/522, 531, 532, 549; 73/1.16, 1.57, 709, 73/714, 753; 604/65–67
See application file for complete search history.

(56) References Cited

U.S. PATENT DOCUMENTS

| | | | | |
|---|---|---|---|---|
| 3,197,068 A | * | 7/1965 | Corbin et al. | 222/59 |
| 3,252,623 A | * | 5/1966 | Corbin et al. | 222/59 |
| 3,450,153 A | * | 6/1969 | Tage et al. | 137/486 |
| 3,456,648 A | * | 7/1969 | Lee et al. | 604/66 |
| 3,655,095 A | * | 4/1972 | Kienitz | 222/39 |
| 3,990,443 A | * | 11/1976 | Fletcher | 604/65 |
| 4,207,871 A | * | 6/1980 | Jenkins | 604/65 |
| 4,375,072 A | * | 2/1983 | Rice | 361/87 |
| 4,652,260 A | * | 3/1987 | Fenton et al. | 604/67 |
| 4,681,563 A | * | 7/1987 | Deckert et al. | 604/67 |
| 4,815,313 A | | 3/1989 | Beard | |
| 4,979,940 A | * | 12/1990 | Bobo et al. | 604/503 |
| 5,087,245 A | * | 2/1992 | Doan | 604/67 |
| 5,242,404 A | * | 9/1993 | Conley et al. | 604/119 |
| 5,256,157 A | * | 10/1993 | Samiotes et al. | 604/246 |
| 5,647,853 A | | 7/1997 | Feldmann et al. | |

(Continued)

FOREIGN PATENT DOCUMENTS

| EP | 0 416 911 A2 | 9/1990 |
|---|---|---|
| EP | 0 824 933 A2 | 2/1998 |

(Continued)

*Primary Examiner* — Patrick Assouad
*Assistant Examiner* — Lamarr Brown
(74) *Attorney, Agent, or Firm* — Dinsmore & Shohl LLP (57) ABSTRACT

An ambulatory infusion device for infusion of a liquid drug into a patient's body over an extended period of time and methods thereof are disclosed. The device includes a sensor assembly, which produces a sensor assembly output based on an infusion characteristic of the ambulatory infusion device and based on a supply voltage/current, and a supply unit which is coupled to a sensor of the sensor assembly and generates the supply voltage/current. A sensor testing unit detects a failure of the sensor assembly, wherein the sensor testing unit is coupled to the sensor assembly and the supply unit, and the sensor testing unit carries out a sensor testing sequence. The sensor testing sequence includes controlling the supply unit so as to produce a variation of the supply voltage/current, and determining whether the variation of the supply voltage/current produces a corresponding variation of the sensor assembly output.

20 Claims, 5 Drawing Sheets

U.S. PATENT DOCUMENTS

| | | | |
|---|---|---|---|
| 5,807,322 A | 9/1998 | Lindsey et al. | |
| 5,919,221 A * | 7/1999 | Miesel | 607/119 |
| 5,935,106 A | 8/1999 | Olsen | |
| 6,485,465 B2 | 11/2002 | Moberg et al. | |
| 6,648,861 B2 | 11/2003 | Platt et al. | |
| 6,659,980 B2 | 12/2003 | Moberg et al. | |
| 7,018,361 B2 | 3/2006 | Gillespie, Jr. et al. | |
| 7,143,646 B2 * | 12/2006 | Kopp et al. | 73/290 R |
| 7,347,836 B2 | 3/2008 | Peterson et al. | |
| 7,644,603 B2 * | 1/2010 | Gordon et al. | 73/1.57 |
| 2001/0034502 A1 * | 10/2001 | Moberg et al. | 604/154 |
| 2002/0147425 A1 * | 10/2002 | Briggs et al. | 604/65 |
| 2003/0073954 A1 * | 4/2003 | Moberg et al. | 604/154 |
| 2003/0233069 A1 * | 12/2003 | Gillespie et al. | 604/131 |
| 2003/0236489 A1 * | 12/2003 | Jacobson et al. | 604/67 |
| 2005/0218904 A1 * | 10/2005 | Shimoyama et al. | 324/522 |
| 2005/0267413 A1 * | 12/2005 | Wang et al. | 604/131 |
| 2006/0079862 A1 * | 4/2006 | Genosar | 604/890.1 |
| 2006/0135907 A1 * | 6/2006 | Remde et al. | 604/67 |
| 2006/0142692 A1 * | 6/2006 | Jacobson et al. | 604/67 |
| 2007/0068269 A1 * | 3/2007 | Lepine et al. | 73/753 |
| 2007/0115005 A1 * | 5/2007 | Shimizu et al. | 324/549 |
| 2007/0149926 A1 | 6/2007 | Moberg et al. | |
| 2007/0176121 A1 * | 8/2007 | Lyons et al. | 250/492.1 |
| 2007/0260174 A1 * | 11/2007 | Jung et al. | 604/65 |
| 2007/0270747 A1 | 11/2007 | Remde | |
| 2007/0293817 A1 * | 12/2007 | Feng et al. | 604/65 |
| 2008/0004567 A1 * | 1/2008 | Susi | 604/67 |
| 2008/0319384 A1 * | 12/2008 | Yodfat et al. | 604/67 |
| 2009/0062767 A1 * | 3/2009 | Van Antwerp et al. | 604/504 |
| 2009/0069743 A1 * | 3/2009 | Krishnamoorthy et al. | 604/66 |
| 2009/0124964 A1 * | 5/2009 | Leach et al. | 604/66 |
| 2009/0131769 A1 * | 5/2009 | Leach et al. | 600/309 |
| 2009/0177148 A1 * | 7/2009 | DelCastilio et al. | 604/67 |
| 2009/0299277 A1 * | 12/2009 | Kamen et al. | 604/67 |
| 2010/0005851 A1 * | 1/2010 | Cottles et al. | 73/1.57 |
| 2010/0030137 A1 * | 2/2010 | Hall et al. | 604/66 |
| 2010/0198143 A1 * | 8/2010 | Estes et al. | 604/66 |
| 2010/0241065 A1 * | 9/2010 | Moberg et al. | 604/67 |
| 2010/0286599 A1 * | 11/2010 | Ziegler et al. | 604/65 |
| 2011/0009812 A1 * | 1/2011 | Brown | 604/31 |
| 2011/0028937 A1 * | 2/2011 | Powers et al. | 604/500 |
| 2011/0040247 A1 * | 2/2011 | Mandro et al. | 604/66 |
| 2011/0137241 A1 * | 6/2011 | DelCastilio et al. | 604/67 |
| 2011/0144574 A1 * | 6/2011 | Kamen et al. | 604/67 |

FOREIGN PATENT DOCUMENTS

| | | |
|---|---|---|
| EP | 0 589 356 A2 | 9/1999 |
| EP | 1 649 884 A1 | 4/2006 |
| EP | 1 652 542 A1 | 5/2006 |
| EP | 1 930 039 A2 | 6/2008 |
| WO | 01/24854 A1 | 4/2001 |
| WO | 03/053498 A2 | 7/2003 |
| WO | 2008/147966 A1 | 12/2008 |

* cited by examiner

AMBULATORY INFUSION DEVICE WITH SENSOR TESTING UNIT

CROSS REFERENCE TO RELATED APPLICATIONS

This patent application claims the benefit of European Patent Application No. EP09005407.3, filed Apr. 16, 2009.

TECHNICAL FIELD

The present disclosure generally relates to an ambulatory infusion device for the infusion of a liquid drug into a patient's body over an extended time period. The infusion device comprises a sensor testing unit for detecting a failure of a sensor assembly of the infusion device. The present disclosure is also directed towards a corresponding method for detecting a failure of a sensor assembly.

BACKGROUND

As background, ambulatory infusion devices for infusion of a liquid drug over an extended time period are known in the art for a number of therapies. In particular, such devices may form the basis for a state-of-the-art therapy for Diabetes Mellitus by CSII (Continuous Subcutaneous Insulin Infusion). Such an ambulatory infusion device is disclosed, for example, in PCT Patent Application Publication No. WO/2003/053498, to which reference is made for the general design and features of such devices according to the state of the art. An ambulatory infusion device according to the technical field as stated above and, more particularly, an ambulatory infusion device in accordance with the present disclosure may be referred to simply as a "device" or an "infusion device."

Besides diabetes therapy, ambulatory infusion devices may be used for a number of other therapies, such as cancer treatment or pain therapy, without requiring substantial modification. Although this disclosure mainly refers to diabetes (i.e., CSII) therapy, it is contemplated that the embodiments shown and described herein may be used for other types of therapies as well, without being limited to this specific application.

SUMMARY

In one embodiment, an ambulatory infusion device for infusion of a liquid drug into a patient's body over an extended period of time comprises: a sensor assembly having a sensor, wherein the sensor assembly produces a sensor assembly output based on an infusion characteristic of the ambulatory infusion device and based on a supply voltage/current; a supply unit, wherein the supply unit is coupled to the sensor and generates the supply voltage/current; and a sensor testing unit which detects a failure of the sensor assembly, wherein the sensor testing unit is coupled to the sensor assembly and the supply unit, and the sensor testing unit carries out a sensor testing sequence, the sensor testing sequence comprising: controlling the supply unit so as to produce a variation of the supply voltage/current, and determining whether the variation of the supply voltage/current produces a corresponding variation of the sensor assembly output.

In another embodiment, a method for detecting a failure of a sensor assembly of an ambulatory infusion device, wherein the sensor assembly comprises a sensor and produces a sensor assembly output based on an infusion characteristic of the ambulatory infusion device and based on a supply voltage/current coupled to the sensor, comprises: producing a variation of the supply voltage/current, and determining whether the variation of the supply voltage/current produces a corresponding variation of the sensor assembly output.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the scope of the claims. The following detailed description of the illustrative embodiments can be understood when read in conjunction with the following drawings, where like structures are indicated with like reference characters and in which:

DETAILED DESCRIPTION

The various embodiments described herein generally relate to ambulatory infusion devices for infusion of a liquid drug into a patient's body over an extended time period. In particular, embodiments herein relate to detecting failure of a sensor (or sensors) used by the infusion device. Such sensors may be used to supervise overall operation of the device and to detect the occurrence of hazardous situations (e.g., fluidic leakages and occlusions). Often devices are of the syringe-driver type and comprise a force sensor as part of the drive system which measures the reaction force that is exerted by the drive system onto the plug of a drug cartridge when infusing the drug contained in the drug cartridge. Alternatively or additionally, infusion devices may comprise a fluidic pressure sensor or a drug flow sensor, for example, at the drug cartridge outlet or directly at the infusion site. Since the primary purpose of such sensors may be the early detection of occlusions (i.e., blockages of the infusion line), they may also be referred to as "occlusion sensors." Proper operation of such occlusion sensors may be important for the overall system and patient safety.

Typically, a sensor in an ambulatory infusion device may be disposed at a position which is remote from the other electronic components (e.g., near the drug cartridge) and therefore may require cabling such as, for example, a flexible printed circuit board, discrete wires, or other suitable means. In some embodiments, the sensor may be a disposable sensor which is connected via releasable electrical connectors (e.g., a sensor at the infusion site). Since cabling, wiring, and connectors have been known to be susceptible to failure (e.g., opens, shorts, damaged wires, loose contacts, intermittent contacts, etc.), it may be desirable to assure the integrity of the sensor output (and, hence, the cabling, wiring, and/or connections to the sensor) and to safely detect any failures.

As one example, U.S. Patent Application Publication No. 2007/0149926 discloses a type of fault detection in a syringe-driver device which compares two independent force measurements. In particular, it is determined whether the level of the motor current (which may be indicative of the infusion force) corresponds to a force signal measured by a force sensor. This approach may be limited in that it is linked to specific hardware architectures and may be dependent on a considerable number of system parameters.

Embodiments of the present disclosure help to improve the operation of ambulatory infusion devices and to ensure reliable, cost-effective detection of failures for many different types of device architectures. Many sensors that are typically used in ambulatory infusion devices (e.g., occlusion sensors, including the subsequent measurement circuitry to which they are connected) produce outputs that are dependent on the supply voltage/current to which the sensor is coupled (e.g., in order to provide an operating voltage or current for the sensor). In accordance with this disclosure, proper operation (or a fault) of the sensor assembly may be detected by varying the supply voltage/current and determining if this variation is properly reflected by a corresponding variation of the sensor assembly output.

For purposes of this disclosure, the term "output" refers to a physical characteristic, such as pressure, force, voltage, current, ohmic resistance, and the like. It also refers to the numeric representation of such a physical characteristic as obtained, for example, by analog-to-digital conversion of such a characteristic. The value of an output may be constant or changing over time. For simplification purposes, a specific value of an output may also be referred to as "output" if the meaning is obvious within the context.

For purposes of this disclosure, the term "infusion characteristic" refers to a physical characteristic or property of the infusion device which is measured by the sensor of the sensor assembly and which is associated with the drug infusion or administration. The infusion characteristic may, for example, include a pressure of the drug or any other physical characteristic which corresponds to the pressure of the drug, such as the reaction force exerted by a drive system of the device.

For purposes of this disclosure, the term "sensor assembly" refers to an electrical sensor for sensing a physical characteristic, in particular an infusion characteristic, and the associated measurement circuitry which is typically used for filtering, amplification, analog-to-digital conversion, and the like. In one embodiment, the sensor may be an occlusion sensor as described above.

For purposes of this disclosure, the term "sensor assembly output" refers to the output which is generated as the overall output of the sensor assembly. The sensor assembly output may include an analog signal (e.g., voltage or current) or a number representing the digitized analog signal output (e.g., digitized by an analog-to-digital converter). The term "sensor output" refers to an output which is generated or varied by the sensor based on the infusion characteristic. Examples of sensor outputs include the electrical current through a force-sensitive resistor (FSR) or the differential voltage of a resistive strain-gauge bridge under mechanical load.

For purposes of this disclosure, the term "supply voltage/current" refers to the output which is generated by a power supply. For a constant voltage power supply, the supply voltage/current refers to the voltage output generated by the power supply. For example, a constant voltage power supply may generate an output of about 3 Volts that may be used to supply power to the sensor and to other circuitry in the infusion device. For a constant current power supply, the supply voltage/current refers to the current output generated by the power supply. For example, a constant current power supply may generate an output of about 4 milliamps that may be used to supply power to the sensor and to other circuitry in the infusion device. For a variable voltage power supply, the supply voltage/current refers to the variable voltage output generated by the power supply. For example, an AC voltage power supply may generate an output of about 12 Volts peak-to-peak at about 60 Hertz that may be used to supply power to the sensor and to other circuitry in the infusion device.

For purposes of this disclosure, the terms "administration of the drug," "administering the drug," and similar syntactical variations refer to the infusion of the drug into the body of the patient.

Figure 1:
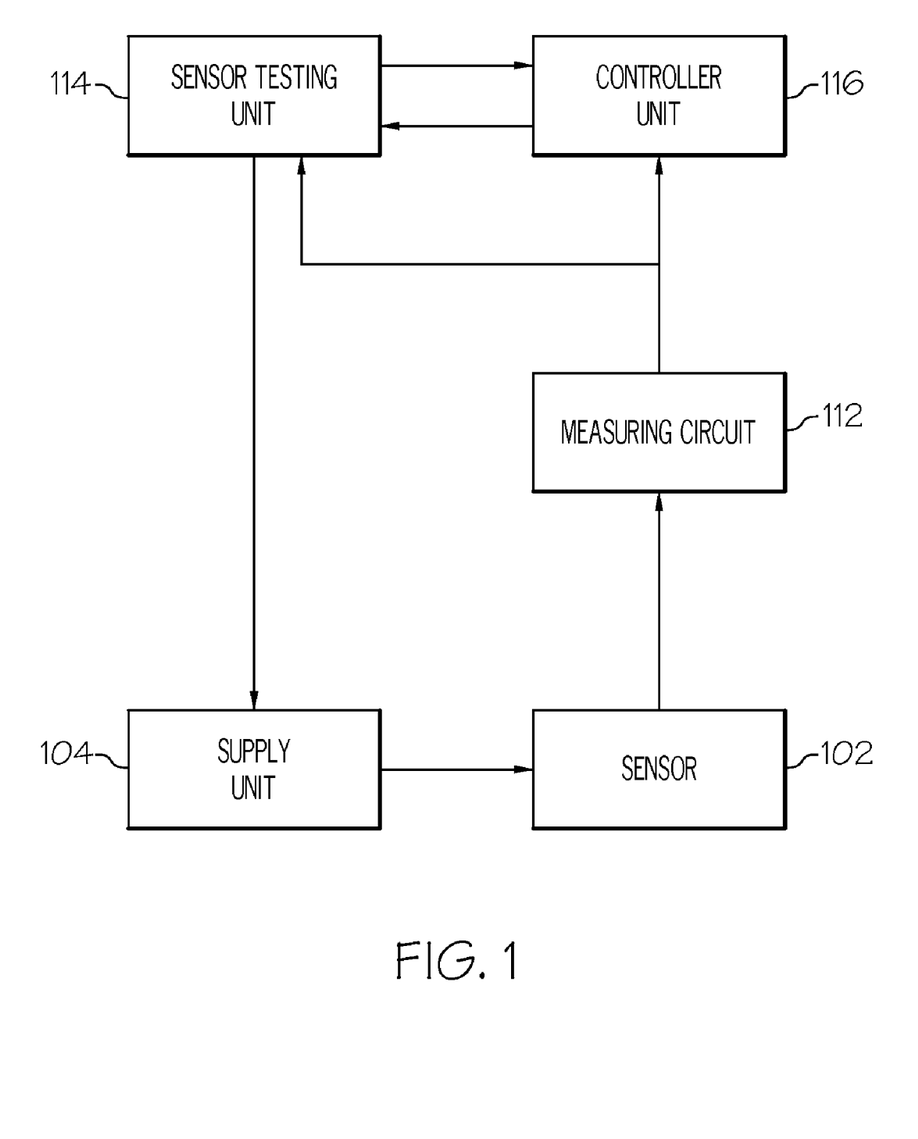
FIG. 1 depicts a block diagram of an ambulatory infusion device according to one or more embodiments shown and described herein.

FIG. 1 shows a block diagram of an infusion device according to one embodiment of the present disclosure. The infusion device comprises a sensor 102, a supply unit 104, measurement circuitry 112, a sensor testing unit 114, and a controller unit 116. The sensor 102 and the measurement circuitry 112, in combination, form the sensor assembly. The controller unit 116 may control and monitor the operation of the infusion device. The controller unit 116 may include state-of-the-art components such as one or more microcontrollers, memory, clock circuitry, interface circuitry, and the like. Other components of the infusion device such as a drive unit, a drug cartridge, a user interface, and the like are not shown in FIG. 1 but are well known for a person skilled in the art. The overall design of the infusion device may, for example, be in accordance with the device as disclosed in PCT Application Publication No. WO/2003/053498 or any commercially-available insulin infusion pump.

The characteristics of the sensor 102 may be assumed to be such that the sensor output is proportional to a supply voltage/current. It may also be assumed that the transfer characteristics of the measurement circuitry 112 are linear, such that the sensor assembly output of the sensor assembly is expected to be proportional to the supply voltage/current as well. None of these assumptions, however, is required as long as the corresponding relationship is unique. For example, there may be a non-linear relationship between the supply voltage/current and the sensor output. However, the sensor testing unit 114 may be able to determine whether the sensor is operating properly as long as the relationship between the supply voltage/current and the sensor output is known.

The supply unit 104 is configured to supply the sensor 102 with the supply voltage/current. As discussed herein, the supply voltage/current may be varied between two discrete levels such as two different supply voltage levels or two different supply current levels. The sensor assembly output may be pre-processed and sampled by the measurement circuitry 112. The measurement circuitry 112 typically comprises pre-processing circuitry such as amplifiers and/or signal conditioning circuitry, a sample-and-hold circuit, and an analog-to-digital converter as is known in the art. The measurement circuitry 112 may couple the sensor assembly output to the sensor testing unit 114 as well as to the controller unit 116. The general evaluation of the sensor assembly output for supervising the administration of the drug and the detection of sensor failures (and other faults) may be performed by the controller unit 116.

For testing the sensor assembly, the sensor testing unit 114 may control the supply unit 104 so as to produce a variation of the supply voltage/current. The sensor testing unit 114 may then be capable of detecting whether or not the variation of the sensor assembly output corresponds to the variation of the supply voltage/current. If this is not the case, the sensor testing unit 114 may send a corresponding fault signal to the controller unit 116 which may initiate fault handling steps such as terminating the drug administration and/or alarming the user via a user interface (e.g., by an optical, acoustical, or tactile signal). Testing of the sensor assembly may be initiated by the controller unit 116 and may be carried out in fixed time intervals such as, for example, every 1 minute or every 3 minutes. In addition or alternatively, the testing may be carried out before, during, and/or after a drug administration.

Figure 2A:
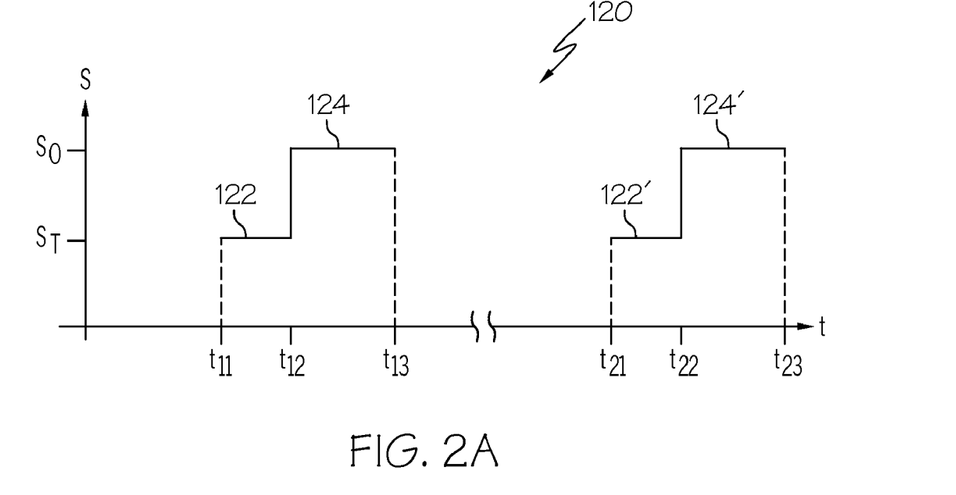
FIGS. 2A-B depict a tester sensing sequence according to one or more embodiments shown and described herein.
Figure 2B:
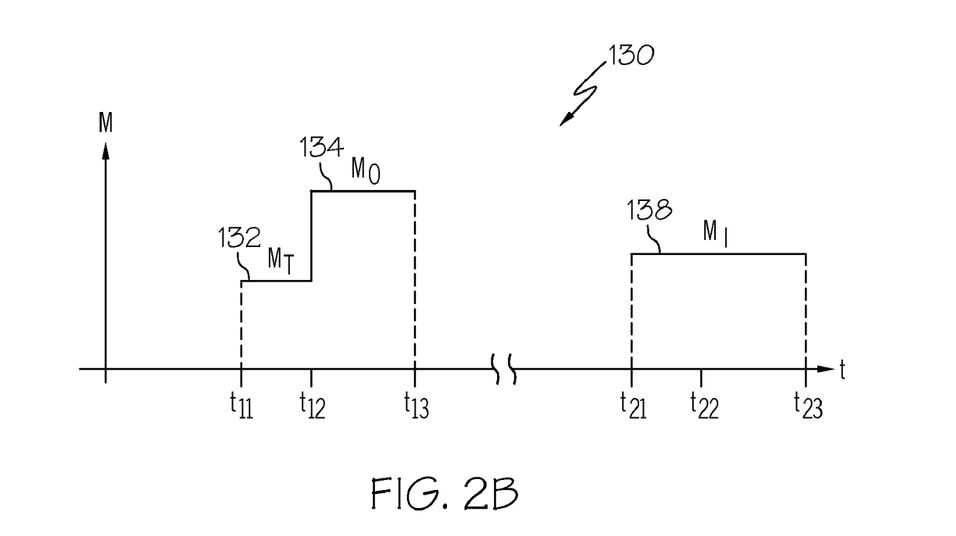

FIGS. 2A and 2B depict a sensor testing sequence according to one embodiment shown and described herein. Graph 120 of FIG. 2A illustrates the supply voltage/current, S, and graph 130 of FIG. 2B illustrates the sensor assembly output, M, both as functions of time, t. As shown in this embodiment, the supply unit 104 may provide two discrete levels of the supply voltage/current S, namely a testing supply level $S_T$ and an operating supply level $S_O$. The operating supply level $S_O$ may be the nominal supply level for which the sensor 102 is designed, and the testing supply level $S_T$ may be half of the operating supply level $S_O$. It to be understood that the testing supply level $S_T$ may comprise other levels as well (e.g., ⅓ or ⅔ of $S_O$), including levels that are higher than the operating supply level $S_O$. Although not shown in FIGS. 2A and 2B, the supply unit 104 may also provide a supply voltage/current level corresponding to the sensor 102 being inactive (e.g., zero voltage or current).

In an initial state, the supply unit 104 may provide a supply voltage/current which results in the sensor 102 being inactive. That is, the supply voltage/current may be zero (e.g., 0 Volts or 0 mA), which may conserve energy by powering down the sensor (and other circuitry as well) when the infusion device is not administering the drug. At a first point in time, $t_{11}$, the supply unit 104 may be controlled by the controller unit 116 to provide the supply voltage/current S at the testing supply level $S_T$, as indicated by line 122. The resulting testing output value $M_T$ is indicated by line 132 and may be sampled (e.g., digitized) by the measurement circuitry 112. At the second point in time, $t_{12}$, the supply unit 104 may be controlled by the controller unit 116 to provide the supply voltage/current S at the operating supply level $S_O$ as indicated by line 124. The resulting operating output value $M_O$ as shown by line 134 may be sampled by the measurement circuitry 112.

The two sampled values $M_T$ and $M_O$ of the sensor assembly output may be evaluated by the sensor testing unit 114 which may determine if the relationship $$\frac{M_T}{S_T} = \frac{M_O}{S_O} \quad \text{(Eq. 1)}$$

or $$\frac{M_T}{M_O} = \frac{S_T}{S_O}$$

is satisfied (i.e., within an expected range). Generally, Eq. 1 indicates the expected relationship between the supply voltage/current and the sensor assembly output when the sensor assembly output is proportional to the supply voltage/current. As can be seen from the graph 130, the change of the level of the supply voltage/current S at time $t_{12}$ is reflected by a proportional change of the level of the sensor assembly output M, thus indicating proper operation of the sensor 102 and the measurement circuitry 112. The sensor 102 may be deactivated at time $t_{13}$ (e.g., to save energy).

After switching the power supply from the testing supply level $S_T$ to the operating supply level $S_O$ at time $t_{12}$, a drug administration may be performed in the time interval from $t_{12}$ to $t_{13}$ (i.e., with the sensor 102 being operated at its nominal supply level). Depending on the specific administration regime of the infusion device, the sensor 102 may be operated continuously during the administration or may be operated in a non-continuous sequence. Additionally or alternatively, the sensor testing sequence may be carried out repeatedly during drug administration.

Continuing to refer to FIGS. 2A and 2B, the sensor testing sequence starting at time $t_{21}$ and ending at time $t_{23}$ shows a situation in which the sensor 102 and/or the measurement circuitry 112 may not be operating properly. As indicated by lines 122', 124', the sensor 102 is consecutively supplied with the testing supply level $S_T$ at time $t_{21}$ and the operating supply level $S_O$ at time $t_{22}$, as described above. However, the sensor assembly output $M_1$ does not reflect this variation of the supply voltage, but stays constant, as indicated by line 138. It is to be noted that, for some types of faults, the sensor assembly output M may show a slight variation such as, for example, due to noise that does not correspond to the variation of the supply voltage/current.

The proportional relation between the supply voltage/current S and the sensor assembly output M according to Eq. 1 may be based on a number of assumptions and idealizations. In particular, it may be assumed that the infusion characteristic such as a mechanical load which is acting on the sensor 102 stays relatively constant during the sensor testing sequence. This is likely since the response time of the mechanical load may be substantially greater than the testing time (e.g., $t_{12}-t_{11}$). Furthermore, it may be assumed that neither the sensor output nor the sensor assembly output M has an offset component, a substantial amount noise, or drift component.

When taking noise effects into account, the sensor testing unit 114 may determine whether the ratio of the sensor assembly output at the different levels of supply voltage/currents fall within an expected range. The limits of the expected range may take into consideration the predicted amount of noise and may be selected to be relatively large in order to avoid false alarms. The expected range may also be selected to be small enough to insure that it is based on the variation of the supply voltage/current S. Also more advanced methods for filtering noise (e.g., statistical hypothesis testing for a given ratio or calculating the difference of the sensor assembly outputs) may be employed as well.

The time delay between taking the samples of the sensor assembly output should be relatively short in order to minimize the superimposed effect of a variation of the infusion characteristic. For the example shown in FIG. 2A, the sampling of the sensor assembly output M may be performed shortly before $t_{12}$ and $t_{22}$ for the testing supply level $S_T$ and shortly after $t_{12}$ and $t_{22}$ for the operating supply level $S_O$. This time delay may be, for example, 1 millisecond.

Referring to FIGS. 1, 2A and 2B, if the infusion device determines (e.g., via the sensor testing unit 114) that a variation of the supply voltage/current is not reflected by a corresponding variation of the sensor assembly output, the presence of a fault in the sensor assembly may be assumed. When a fault is detected, the infusion device may be configured to carry out fault handling steps such as, for example, stopping the drug administration and alerting the user by an optical, acoustical, and/or tactile alarm.

The infusion device may detect the presence of a fault after a single sensor testing sequence. However, since unwanted disturbances may be inadvertently introduced into the sensor assembly output, the infusion device may be configured to assume the presence of a fault only if the fault persists for a consecutive number of testing sequences. Such unwanted disturbances may be introduced into the sensor 102 and/or the sensor assembly output by electrical or mechanical means such as, for example, electrical noise, electromagnetic interference, shock, vibration, and so forth. In one embodiment, the sensor testing unit 114 may be configured to repeat the sensor testing sequence at least one additional time if the first sensor testing sequence indicates the presence of a fault.

The expected and corresponding variation of the sensor assembly output when the supply voltage/current is varied may be determined by the design of the sensor and its physical operation principle as well as the subsequent measurement circuitry as discussed herein. The output of some sensors may vary linearly when the supply voltage/current is varied, while the output of other sensors may vary non-linearly when the supply voltage/current is varied. Thus, an expected range of the variation of the sensor assembly output may be established, if necessary.

In some embodiments, the sensor assembly comprises a sensor 102 with at least one force-sensitive resistor, pressure-sensitive resistor, and/or strain gauge. A force-sensitive resistor (FSR) may, for example, be coupled to the drive system of the infusion device according to the disclosure of U.S. Pat. No. 6,485,465. Alternatively, a bending beam and strain gauge arrangement may be used for the force measurement. In some embodiments, the sensor assembly comprises a strain-gauge measurement bridge for measuring the reaction force, for which a corresponding design is disclosed in PCT Patent Application No. WO/2001/24854. The sensor 102 may be advantageously mechanically and/or electrically pre-loaded to always ensure a non-zero sensor output signal.

In some embodiments, the supply unit 104 may comprise a variable voltage supply or a variable current supply, depending on the type of the sensor used. Accordingly, in one embodiment, the supply voltage/current may be a supply current if the sensor is designed for controlled current supply or may be a supply voltage if the sensor is configured for controlled voltage supply. Both kinds of sensors are known in the art and are commercially available in a large variety.

As shown in FIGS. 2A and 2B, the supply unit 104 may be configured to provide a set of at least two discrete levels of the supply voltage/current, such as different supply voltage levels or supply current levels. This may be achieved by various means such as using at least two power supplies. It may alternatively be achieved by a combination of one supply and additional resistors, such as dropping resistors or shunts, and a supply selector which is controlled by the sensor testing unit for switching between the levels in order to vary the supply voltage/current. The supply selector may comprise solid state circuit such as a multiplexer.

As discussed herein, the operating supply level may be the standard supply level for which the sensor is designed and may be normally used for measuring the infusion characteristic (e.g., when the infusion device is administering the drug to the patient). For this type of embodiment, the sensor testing sequence may comprise switching the supply voltage/current between the two discrete supply levels one or more times. The corresponding graphical representation of the supply voltage/current may be a step or a square wave.

As an alternative to two supply levels, the supply unit 104 may be configured to provide three or more discrete supply levels, and the sensor testing sequence may comprise switching between these multiple supply levels when varying the supply voltage/current. In another embodiment, the supply unit 104 may be configured to provide a continuously varying supply voltage/current, for example, of the sinusoidal wave type or the triangular wave type. In this disclosure, two discrete supply levels are shown and described, although it is to be understood that more than two discrete supply levels may be used. The modifications required for three or more discrete supply levels or for a continuously varying supply voltage/current are known in the art.

In some embodiments, the expected variation of the sensor assembly output when the supply voltage/current is varied may be proportional to the variation of the supply voltage/current. Several types of sensors generate an output which is directly or inversely proportional to the level of the supply voltage/current. This may be the case, for example, for the current through an FSR when the FSR is supplied with a fixed voltage, or for the voltage drop across an FSR when the FSR is supplied with a fixed current. This may also be the case for the differential voltage across sensor bridge when the sensor bridge is supplied by a fixed voltage or current. The sensor assembly output may also be proportional to the variation of the supply voltage/current for the rectified output of capacitive sensors, inductive sensors, or sensor bridges when supplied by a sinusoidal AC supply.

If the sensor output is proportional to a supply voltage/current, the sensor assembly output may also be proportional to the supply voltage/current, assuming the measurement circuitry 112 is linear. In case of an offset (e.g., voltage or current offset), the absolute value of the sensor assembly output may not be directly proportional to the absolute value of the supply voltage/current. The expected variation of the sensor assembly output, however, may be proportional to the variation of the supply voltage/current if the offset is taken into consideration. If the sensor 102 exhibits substantially non-linear characteristic, the measurement circuitry 112 may compensate for this by applying linearization techniques known in the art. As discussed herein, an expected proportional relationship may allow the sensor testing unit to determine if the variation of the supply voltage/current is reflected in the expected variation of the sensor assembly output by simple mathematical (e.g., division) operations.

In some embodiments, the sensor testing unit 114 may be configured to measure the value of the supply voltage/current. Measuring the actual value of the supply voltage/current may be advantageous for more accurately determining the relationship between the variation of the supply voltage/current and the sensor assembly output. This may be the case if the supply voltage/current can vary, for example, if the power supply is a battery and/or if the level of the supply voltage/current can be influenced by the sensor or other factors. An example of such a power supply may be a constant voltage power supply having a non-negligible internal series impedance which supplies power to an FSR.

In some embodiments, varying the supply voltage/current may be carried out by switching a single power supply between at least two discrete supply voltage/current levels (e.g., at least two discrete voltage or current levels). The supply voltage/current may, as discussed herein, be a supply voltage or a supply current. The switching may be performed by selecting one of at least two independent supplies or by varying a single supply. Alternatively, the sensor testing sequence may comprise varying the supply voltage/current continuously by providing, for example, a sinusoidal wave or triangle wave voltage or current supply.

In some embodiments, the expected variation of the sensor assembly output upon a variation of the supply voltage/current may be proportional to the variation of the supply voltage/current. For those embodiments, the sensor testing sequence may comprise determining whether the variation of the sensor assembly output is proportional to the variation of the supply voltage/current. For example, the supply unit may generate a supply voltage/current of 3 V, which produces a sensor assembly output of about 1 V; the supply voltage/current may be varied to be about 1.5 V, which produces a sensor assembly output of about 0.5 V. In this example, the sensor assembly output is proportional to the supply voltage/current (i.e., 3V/1.5V=1V/0.5V).

In some embodiments, the sensor testing sequence comprises varying the supply voltage/current such that the expected variation of the sensor assembly output is relatively large as compared to a variation of the sensor assembly output resulting from a variation of the infusion characteristic while carrying out the sensor testing sequence. This implies that the variation of the supply voltage/current should be large and that the steps of varying the supply voltage/current and sampling the sensor assembly output should be carried out in a time interval which is short as compared to the expected variation of the measurement signal. For noise reducing purposes, the sensor testing may further comprise repeatedly varying the supply voltage/current and sampling the sensor assembly output as will be described below in more detail.

For improved immunity to noise, it may be advantageous to expect the variation of the output signal to be within an expected range rather than having a precisely defined value. The limits of such an expected range may depend on the expected level of noise and/or distortion. For such an embodiment, the variation of the output signal corresponds to the variation of the supply voltage/current if it is within the expected range.

In some embodiments, sensor testing may be carried out in defined time intervals prior to, during, and/or after drug administration by the infusion device. The defined time intervals may be short enough to detect a fault of the sensor assembly without significant delay, for example, every second, every minute, or every three minutes. For devices which do not administer the drug continuously but are configured to administer drug boli on demand and/or to administer drug continuously in a pulsed fashion (e.g., with a drug pulse being administered with time intervals of several minutes), the sensor testing may be carried out prior to and/or after the drug administration. If larger drug amounts, such as drug boli, are administered by administering separated drug pulses, a sensor testing sequence may additionally or alternatively be carried out between the administrations of the single drug pulses.

Figure 3A:
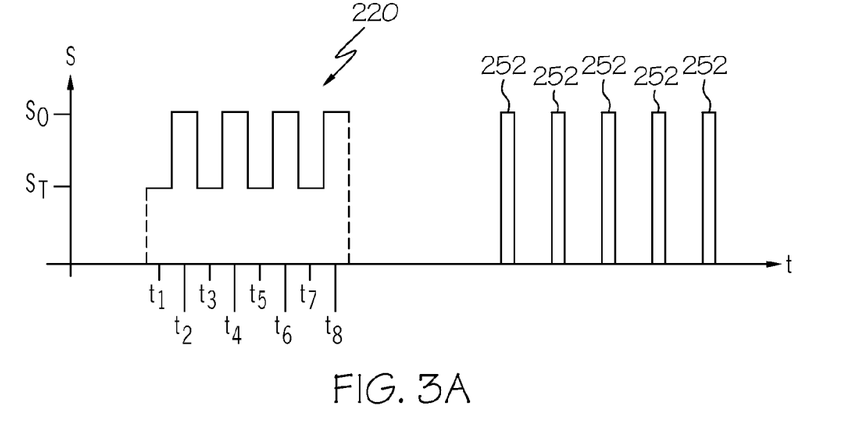
FIGS. 3A-C depict graphs of a supply voltage/current and a sensor assembly output according to one or more embodiments shown and described herein.
Figure 3B:
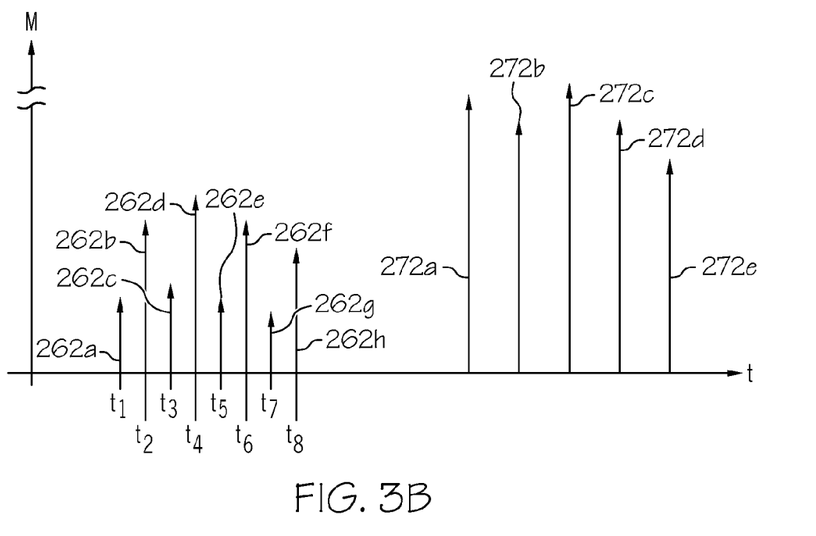
Figure 3C:
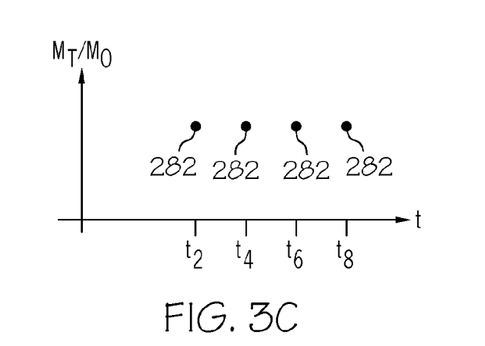

FIGS. 3A-C depict graphs of the supply voltage/current and a sensor assembly output according to the system of FIG. 1 in which the immunity to noise is increased by averaging multiple samples. Graph 220 of FIG. 3A illustrates the supply voltage/current S as a function of time t. The supply unit 104 is controlled so as to repeatedly supply the sensor 102 with the testing supply level $S_T$ followed by the operating supply level $S_O$. This results in an overall square wave signal with the times $t_1, t_2, \ldots, t_8$ indicating the middle of each segment. As shown in FIG. 3B, the sensor assembly output M may be sampled at the times $t_1, t_2, \ldots, t_8$, as shown by sampling arrows 262a, 262b, . . . , 262h. The values sampled at the times $t_1, t_3, t_5, t_7$ are testing output values $M_T$ while the values sampled at the times $t_2, t_4, t_6, t_8$ are operating output values $M_O$. Arrows in FIG. 3B indicate a sample of M with the length of the arrow corresponding to the amplitude of the sampled value. It can be seen that the sampled values of the sensor assembly output M generally reflect the variation of the supply voltage/current S. However, the value of the sensor assembly output M may not be precisely constant at either of the supply voltage/current levels, but may show some additional variation due to noise.

The values of the sensor assembly output M sampled in adjacent segments of the supply voltage/current S may be evaluated pair wise. Therefore, the sensor testing unit 114 may compute an average of $M_T/M_O$ as follows:

$$\frac{M_T}{M_O}(avg) = \frac{1}{4}\left(\frac{M_{T(t_1)}}{M_{O(t_2)}} + \frac{M_{T(t_3)}}{M_{O(t_4)}} + \frac{M_{T(t_5)}}{M_{O(t_6)}} + \frac{M_{T(t_7)}}{M_{O(t_8)}}\right).$$

Because many noise effects and in particular variations of the infusion characteristic may occur slowly in comparison with switching the level of the supply voltage/current S and because taking adjacent samples of the sensor assembly output M, the ratio $M_T/M_O$ may largely be independent of those effects as shown by the dots 282 in FIG. 3C. The dots indicate the computed quotients $M_T/M_O$ according to the formula given above.

In another embodiment, the averaging may be performed such that a ratio is calculated for each $M_T$ using the adjacent $M_O$ on either side, and likewise a ratio is calculated for each $M_O$ using the adjacent $M_T$ on either side. Duplicate ratios are discarded. Therefore, the sensor testing unit 114 may compute an average of $M_T/M_O$ as follows:

$$\frac{M_T}{M_O}(avg) =$$

$$\frac{1}{7}\left(\frac{M_{T(t_1)}}{M_{O(t_2)}} + \frac{M_{T(t_3)}}{M_{O(t_2)}} + \frac{M_{T(t_3)}}{M_{O(t_4)}} + \frac{M_{T(t_5)}}{M_{O(t_4)}} + \frac{M_{T(t_5)}}{M_{O(t_6)}} + \frac{M_{T(t_7)}}{M_{O(t_6)}} + \frac{M_{T(t_7)}}{M_{O(t_8)}}\right)$$

are computed. That is, except the first and last samples, each sampled value of the sensor assembly output M is used for the computation of two $M_T/M_O$ ratios. More advanced filtering and noise reduction techniques may be used as well, but may not be required.

As further illustrated in FIGS. 3A-B, a series of five consecutive drug pulses may be administered by the infusion device after completing the sensor testing sequence (e.g., after $t_8$). For the administration of each of the drug pulses, the sensor 102 may be temporarily supplied with the operating supply level $S_O$ as indicated by the pulses 252. During or after completing the administration of each drug pulse, the infusion characteristic may be determined by sampling the sensor assembly output M, as indicated by the sampling arrows 272a, 272b, . . . , 272e, followed by an evaluation in the controller unit 116. The shown variation of the sampled measurement currents may be typical of the infusion characteristic, particular of the force or pressure which is acting on the sensor 102 during administration of the drug.

In the embodiments of FIGS. 2A, 2B, and 3A, the testing supply level $S_T$ is depicted as about half of the operating supply level $S_O$. Accordingly, the expected testing output value $M_T$ may also be half of the operating output value $M_O$. It will the appreciated by a person skilled in the art that other ratios of the testing supply level $S_T$ and the operating supply level $S_O$ may be used as well, and that the testing supply level $S_T$ may also be higher than the operating supply level $S_O$. It will further be appreciated that the device and the testing method may be modified in a straightforward way so as to have more than two levels of the supply signal or have a continuous variation of the supply signal (e.g., a sine wave or a triangular wave).

Figure 4:
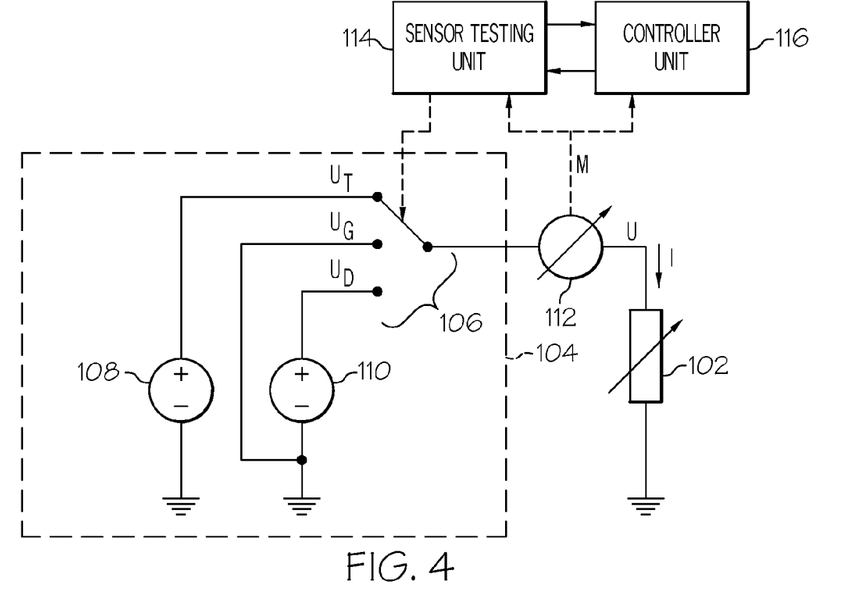
FIG. 4 depicts a schematic of an ambulatory infusion device according to one or more embodiments shown and described herein.

FIG. 4 depicts a more detailed view of a hardware structure for the system of FIG. 1. The sensor 102 may comprise an FSR which measures the reaction force exerted on the drug in the drug container (not shown) as disclosed, for example, in U.S. Pat. No. 6,485,465. Alternatively, the sensor 102 may be a pressure sensitive resistor which measures the fluidic pressure of the drug at the outlet of the drug cartridge or may be a strain gauge which is mounted onto a bending beam. In this embodiment, the supply voltage U which is supplied to the sensor 102 is the supply voltage/current S and the resulting current I through the sensor 102 is the sensor output. The measurement circuitry 112 may comprise a current-to-voltage converter followed by an analog-to-digital converter (ADC), such that the output signal M is a number which is proportional the current I through the sensor 102 when the sensor assembly operates properly. For a constant value of the infusion characteristic, that is, the mechanical load which is acting on the sensor 102, and thus a given ohmic resistance of the sensor 102, the current I may be proportional to the supply voltage. The resistance of the sensor 102 may be either directly or inversely proportional to the acting force or pressure or may have any defined non-linear characteristics.

In the embodiment shown in FIG. 4, the supply unit 104 may comprise a testing voltage supply 108 for providing a testing supply voltage $U_T$ and an operating voltage supply 110 for providing an operating supply voltage $U_O$. These voltages correspond to the testing supply level $S_T$ and the operating supply level $S_O$ as described above. The supply unit 104 may further comprise a supply selector 106 for alternatively connecting the sensor 102 to either of the testing voltage supply 108, the operating voltage supply 110, or ground $U_G$. The voltage supplies 108, 110 may be two different voltage supplies as shown in FIG. 4 or may alternatively be implemented as a single variable voltage supply. In either case, the sensor testing unit 114 may control (e.g., via the supply selector 106 or other suitable means) the voltage supply to the sensor 102 to be either the testing supply voltage $U_T$, the operating supply voltage $U_O$, or ground $U_G$. If more than two levels of testing supply voltage are used, the sensor testing unit 114 may control the voltage supply to the sensor 102 to be any one of the levels of the testing supply voltage.

The testing supply voltage $U_T$ and the operating supply voltage $U_O$ may be selected in accordance with the sensor specification such that the sensor output is always valid (e.g., readable) by the measurement circuitry 112. In a typical embodiment, the measurement circuitry 112 comprises an operational amplifier and an ADC with a unipolar power supply (i.e., a positive voltage supply with respect to ground), as described below in more detail with reference to FIG. 5. In this case, the amplifier and the ADC may only be capable of processing positive voltage inputs within a certain range (and not inputs which are negative). For this type of embodiment, a testing supply voltage $U_T$ which is in a range of ⅓ to ⅔ of the operating supply voltage $U_O$ may be used. However, if the measurement circuitry 112 is supplied with a bipolar supply voltage with respect to ground, the ADC may be capable of processing both positive and negative inputs.

Instead of the constant voltage supplies 108, 110 shown in FIG. 4, constant current supplies may be used to alternatively supply the sensor 102 with a testing supply current and an operating supply current. In this case, the voltage drop across the sensor 102 may be used as sensor output and the measurement circuitry 112 may be configured to sample and measure this voltage drop. For selecting the operating supply level and the testing supply level, the same considerations as given for a voltage supply hold true. Furthermore, a variable voltage or current supply may be used in which the voltage or current, respectively, varies with time (e.g., a sinusoidal or triangular wave output).

Figure 5:
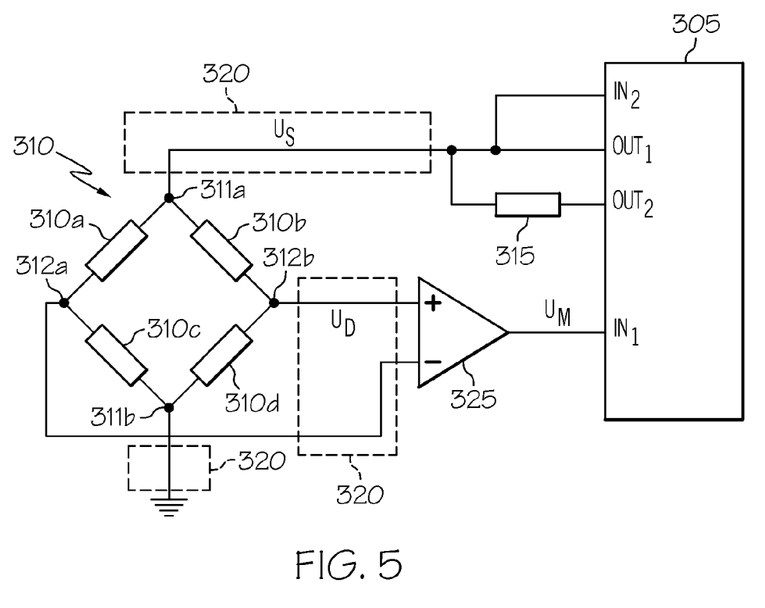
FIG. 5 depicts a schematic of an ambulatory infusion device according to one or more embodiments shown and described herein.

FIG. 5 schematically shows the hardware structure of another exemplary device in accordance with this disclosure. With respect to the operation, reference is additionally made to FIGS. 2A, 2B, and 3A as well as the corresponding description as given above. The sensor of this embodiment may be realized as resistive strain-gauge bridge 310 which comprises resistors 310a, 310b, 310c, 310d having resistances $R_{310a}$, $R_{310b}$, $R_{310c}$, $R_{310d}$, respectively The resistors may be assembled on a bending beam carrier by adhesive bonding, thick-film technologies, or other suitable method. The strain-gauge bridge 310 may be supplied via a pair of opposed supply connectors 311a, 311b with a supply voltage $U_S$ (e.g., supply connector 311a is connected to $U_S$, and supply connector 311b is connected to ground). The differential voltage $U_D$, which may be measured between the other pair of opposed connectors 312a, 312b, may be the sensor output. The overall bridge resistance $R_B$ between the supply connectors 311a, 311b is typically in a range of 5 kilohms to 100 kilohms.

For this embodiment, the ambulatory infusion device may be of the syringe-driver type, and resistors 310a, 310b, 310d, 310d may be part of a strain-gauge beam arrangement, which measures the reaction force which is exerted by a drive system onto the plug of a drug cartridge in the infusion device. An example of a corresponding mechanical structure is disclosed in PCT Patent Application Publication No. WO/2001/024854. Alternatively, the strain-gauge bridge 310 may be part of a fluidic drug pressure sensor. Advantageously, the strain-gauge bridge 310 may be mechanically pre-loaded. The device may further comprise a microcontroller 305 which may integrate major components of the controller unit of the infusion device, the sensor testing unit, as well as part of the supply unit and the measurement circuitry. This may become more readily apparent in the following description.

The resistors 310a, 310b, 310d, 310d may be arranged such that the bridge resistance $R_B$ which can be measured between the supply connectors 311a, 311b stays substantially constant while the resistances $R_{310a}$, $R_{310b}$, $R_{310c}$, $R_{310d}$ depend on the mechanical load that is acting on the sensor. For this arrangement, the ratio $U_D/U_S$ (i.e., the differential voltage $U_D$ of the sensor output divided by the supply voltage $U_S$ as the supply voltage/current) is proportional to mechanical load that is acting on the bridge, independent of the absolute value of the supply voltage $U_S$. The differential voltage $U_D$ may be amplified by an amplifier circuit 325 which comprise an instrumentation amplifier or one or more operational amplifiers. The output of the amplifier circuit 325 generates an output voltage $U_M$ (i.e., with respect to ground). The output voltage $U_M$ may be fed into an analog input $IN_1$ of the microcontroller 305 and may be sampled and digitized by an ADC, for example a 12-bit ADC which may be integrated with the microcontroller 305. The output of the ADC may form the sensor assembly output M (e.g., within the microcontroller 305).

The microcontroller 305 may comprise two voltage output ports $OUT_1$, $OUT_2$, to which the strain-gauge bridge 310 may alternatively supplied. If either of the outputs $OUT_1$, $OUT_2$ is active and provides an output voltage, the other of the two outputs may reconfigured to be in an inactive state, a high-impedance state, or an input port. The two output ports $OUT_1$, $OUT_2$ may provide the same standard supply voltage $U_0$ which is given by or derived from the power supply voltage of the infusion device (and the microcontroller 305) and may, for example, be about 3 V for typical state-of-the-art technology. If the output port $OUT_1$ is active, the standard supply voltage $U_0$ is directly connected to the strain-gauge bridge 310 as operating supply voltage $U_O$. If the output port $OUT_2$ is active, the standard supply voltage $U_0$ is connected via an additional dropping resistor 315 of constant resistance $R_D$ as testing supply voltage $U_T$. The resistance $R_D$ of the dropping resistor 315 is typically chosen to have a similar value as the bridge resistance $R_B$.

If the strain-gauge bridge 310 is supplied via the dropping resistor 315, the dropping resistor 315 and the strain-gauge bridge 310, in combination, form a voltage divider for the output voltage $U_O$ as provided by the microcontroller 305. With $R_B$ being the bridge resistance, the testing supply voltage $U_T$ is accordingly given by:

$$U_T = U_O \times r$$

and $$r = \frac{R_B}{R_B + R_D}$$

with r being a reduction factor. The voltage divider may be substantially symmetrical if the condition $R_D \approx R_B$ is fulfilled. When the sensor assembly operates properly, the differential voltage $U_D$, the output voltage $U_M$ and, thus, the sensor assembly outputs M may be reduced by the same reduction factor r as the supply voltage $U_S$ when the supply is switched from output $OUT_1$ to output $OUT_2$. This may correspond to the expected proportional relationship given by Eq. 1 above. In this embodiment, the supply voltage/current is a supply voltage provided by the microcontroller 305 (i.e., via $OUT_1$ and $OUT_2$). The operating supply level $S_O$ is given by the standard supply voltage $U_O$ and the testing supply level $S_T$ is given by $r \times U_O$ due to the voltage drop introduced by the dropping resistor 315.

In practice, the nominal resistances of the resistors 310a, 310b, 310c, 310d, that is, the resistances in the unloaded state of the strain-gauge bridge 310, may have a considerable manufacturing tolerance. In addition, the standard supply voltage $U_O$ may not be constant over time. Therefore, the supply voltage $U_S$ may additionally be measured via a second analog input $IN_2$ of the microcontroller 305 and this measured voltage may be used for the computation. This may reduce or eliminate any noise or uncertainty introduced by the supply voltage/current.

Most of the components of FIG. 5 may be typically arranged on one or multiple printed circuit boards of the device. The strain-gauge bridge 310 may be connected with the other components via wiring elements such as Flexible Printed Circuit Board (Flexprint), a Flexible Cable Connector (FCC) or via single cables, as indicated by the dashed boxes 320. Those wiring elements may be assembled in a bent condition and, therefore, in stress-loaded state according to the overall design and the arrangements of the components of the infusion device. Alternatively, the amplifier circuit 325 may be disposed at the strain-gauge bridge 310. In this case, the output $U_M$ of the amplifier circuit 325 may be connected with the microcontroller 305 via wiring components. Wiring components as well as soldered connections are known to be particularly susceptible to loose contacts as well as opens and shorts. In a design according to FIG. 5, the occurrence of such a failure results in the input of the amplifier circuit 325 floating (i.e., not being actively driven to a known state) and the measurement voltage $U_M$ as sensor assembly output of the amplifier circuit 325 therefore not properly reflecting a corresponding variation of the supply voltage U as expected. Similarly, the sensor assembly output will not properly reflect the variation of the supply voltage/current if any other component of the sensor assembly, in particular the amplifier circuit 325, the strain-gauge bridge 310 or the ADCs of the microcontroller 305 has an electrical failure.

It can be seen that the embodiment of the disclosure as shown in FIG. 5 requires only one additional hardware component, namely the dropping resistor 315. Implementation of the method for verifying correct operation of the sensor assembly is performed by some basic computational steps which are implemented in the microcontroller 305 (e.g., computer instructions executed by the microcontroller 305). Accordingly, proper operation (or a failure) of the sensor assembly may be detected with little additional hardware and software effort, thus keeping the cost to a minimum.

Figure 6A:
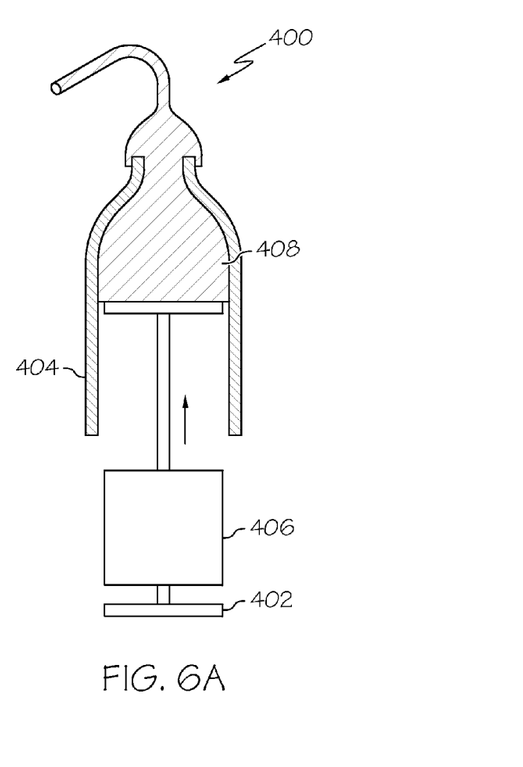
FIGS. 6A-B depict ambulatory infusion devices according to one or more embodiments shown and described herein.
Figure 6B:
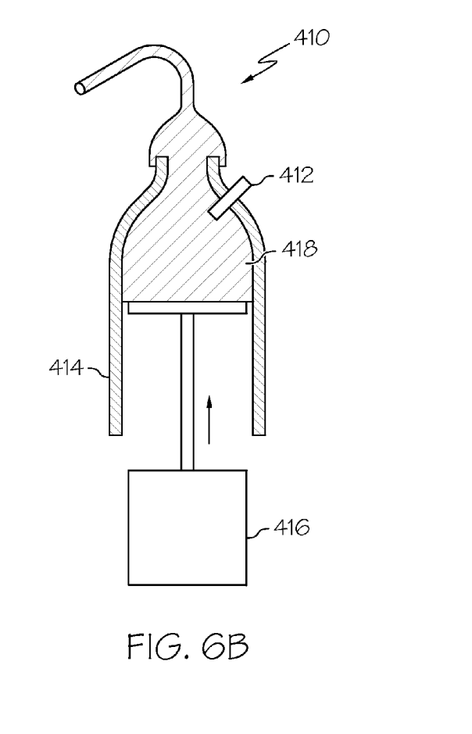

FIGS. 6A and 6B depict examples of ambulatory infusion devices 400, 410 which have a sensor 402, 412 configured to measure an infusion characteristic thereof. In FIG. 6A, the infusion device 400 comprises a sensor 402, a drug cartridge 404 having a liquid drug 408, and a drive mechanism 406. When administrating the liquid drug 408, the drive mechanism 406 may produce a force which pushes the liquid drug 408 out of the drug cartridge 404 and into the body of the patient (not shown). In this embodiment, the sensor 402 may be coupled to the drive mechanism 406 so as to measure a force exerted by the drive mechanism 406 when administering the drug. The use of the sensor 402 in this fashion may, as explained herein, permits the infusion device 400 to determine whether an occlusion has occurred. Thus, the sensor 402 may be capable of measuring a force, which corresponds to an infusion characteristic of the infusion device 400.

Similarly, in FIG. 6B, the infusion device 410 comprises a sensor 412, a drug cartridge 414 having a liquid drug 418, and a drive mechanism 416. When administrating the liquid drug 418, the drive mechanism 416 may produce a force which pushes the drug out of the drug cartridge 414 and into the body of the patient (not shown). In this embodiment, the sensor 412 may be coupled to the drug cartridge 414 so as to measure a pressure of the drug when the infusion device administers the drug. The use of the sensor 412 in this fashion, as explained herein, may permit the infusion device 410 to determine whether an occlusion has occurred. Thus, the sensor 412 may be capable of measuring a pressure, which corresponds to an infusion characteristic of the infusion device 410. These are just two examples of infusions devices which may use the sensor testing methods and systems described herein to determine whether one or more sensors are operating properly. It is contemplated that the embodiments described herein may be used for other types of infusion devices as well.

According to another aspect of this disclosure, the goal of improving the operation of ambulatory infusion devices may be achieved by providing a method for detecting a failure of a sensor assembly of the ambulatory infusion device by carrying out a sensor testing sequence. The sensor assembly may be configured to provide a sensor assembly output based on an infusion characteristic and a supply voltage/current provided to a sensor of the sensor assembly. The sensor testing sequence may comprise the steps of: producing a variation of the supply voltage/current, and determining whether the variation of supply voltage/current produces a corresponding variation of the sensor assembly output. In one embodiment, the method further may comprise the step of sampling the sensor assembly output at different levels of the supply voltage/current such as, for example, two discrete levels of the supply voltage/current.

While particular embodiments and aspects have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. An ambulatory infusion device for infusion of a liquid drug into a patient's body over an extended period of time, the ambulatory infusion device comprising:
    a sensor assembly having a sensor, wherein the sensor assembly produces a sensor assembly output based on an infusion characteristic of the ambulatory infusion device and based on a supply voltage/current;
    a supply unit, wherein the supply unit is coupled to the sensor and generates the supply voltage/current; and
    a sensor testing unit which detects a failure of the sensor assembly, wherein the sensor testing unit is coupled to the sensor assembly and the supply unit, and the sensor testing unit carries out a sensor testing sequence, the sensor testing sequence comprising:
        controlling the supply unit so as to produce a variation of the supply voltage/current, and
        determining whether the variation of the supply voltage/current produces a corresponding variation of the sensor assembly output.

2. The ambulatory infusion device of claim 1, wherein the infusion characteristic is a pressure of the liquid drug or a characteristic corresponding to the pressure of the liquid drug.

3. The ambulatory infusion device of claim 1, wherein the supply unit comprises a variable voltage supply or a variable current supply.

4. The ambulatory infusion device of claim 1, wherein the variation of the supply voltage/current comprises two or more discrete levels of the supply voltage/current.

5. The ambulatory infusion device of claim 1, wherein the variation of the supply voltage/current comprises two discrete levels of the supply voltage/current, a first discrete level and a second discrete level.

6. The ambulatory infusion device of claim 5, wherein the first discrete level is about two times higher than the second discrete level.

7. The ambulatory infusion device of claim 5, wherein the supply unit comprises at least one dropping resistor used for producing the second discrete level.

8. The ambulatory infusion device of claim 1, wherein the supply unit generates a continuously variable supply voltage/current.

9. The ambulatory infusion device of claim 1, wherein determining whether the variation of the supply voltage/current produces a corresponding variation of the sensor assembly output comprises determining whether the corresponding variation of the sensor assembly output is proportional to the variation of the supply voltage/current.

10. The ambulatory infusion device of claim 1, wherein determining whether the variation of the supply voltage/current produces a corresponding variation of the sensor assembly output comprises determining whether the corresponding variation of the sensor assembly output falls within an expected range.

11. The ambulatory infusion device of claim 1, wherein the sensor comprises at least one force-sensitive resistor, pressure-sensitive a resistor, or strain gauge.

12. The ambulatory infusion device of claim 1, wherein the sensor testing unit measures a value of the supply voltage/current.

13. The ambulatory infusion device of claim 1, wherein determining whether the variation of the supply voltage/current produces a corresponding variation of the sensor assembly output comprises averaging two or more samples of the sensor assembly output.

14. The ambulatory infusion device of claim 1, wherein the sensor testing unit comprises a microcontroller having an analog-to-digital converter, the sensor assembly output is coupled to the analog-to-digital converter, and the analog-to-digital converter measures the corresponding variation of the sensor assembly output.

15. A method for detecting a failure of a sensor assembly of an ambulatory infusion device, wherein the sensor assembly comprises a sensor and produces a sensor assembly output based on an infusion characteristic of the ambulatory infusion device and based on a supply voltage/current coupled to the sensor, the method comprising:
    producing a variation of the supply voltage/current, and
    determining whether the variation of the supply voltage/current produces a corresponding variation of the sensor assembly output.

16. The method of claim 15, wherein producing a variation of the supply voltage/current comprises switching a value of the supply voltage/current between at least two discrete supply levels.

17. The method of claim 15, wherein determining whether the variation of the supply voltage/current produces a corresponding variation of the sensor assembly output comprises determining whether the corresponding variation of the sensor assembly output is proportional to the variation of the supply voltage/current.

18. The method of claim 15, wherein producing a variation of the supply voltage/current is performed such that the corresponding variation of the sensor assembly output is relatively large as compared to a variation of the sensor assembly output resulting from a variation of the infusion characteristic.

19. The method of claim 15, wherein acts of the method are carried out in defined time intervals prior to, during, or after drug administration by the ambulatory infusion device.

20. The method of claim 15, wherein the sensor comprises at least one force-sensitive, pressure-sensitive resistor, or strain gauge.

* * * * *

UNITED STATES PATENT AND TRADEMARK OFFICE
CERTIFICATE OF CORRECTION

| | |
|---|---|
| PATENT NO. | : 8,373,421 B2 |
| APPLICATION NO. | : 12/761445 |
| DATED | : February 12, 2013 |
| INVENTOR(S) | : Stefan Lindegger et al. |

It is certified that error appears in the above-identified patent and that said Letters Patent is hereby corrected as shown below:

Title Page:

Item 30, Foreign Application Priority Data, "EP 09005407" should read --EP 09005407.3--;

In the Specification:

Col. 5, Line 20, "It to be understood" should read --It is to be understood--;

Col. 6, Line 15, "$M_1$" should read --$M_I$--;

Col. 10, Line 54, "It will the appreciated" should read --It will be appreciated--;

Col. 12, Line 5, "respectively" should read --respectively.--;

Col. 12, Line 55, "may alternatively supplied" should read --may alternatively be supplied--;

Col. 12, Line 57, "may reconfigured" should read --may be reconfigured--;

Col. 14, Line 18, "When administrating the liquid drug" should read --When administering the liquid drug--;

Col. 14, Line 25, "may, as explained herein, permits" should read --may, as explained herein, permit--;

Col. 14, Line 31, "When administrating the liquid drug" should read --When administering the liquid drug--; and Col. 14, Line 42, "infusions devices" should read --infusion devices--.

Signed and Sealed this
First Day of October, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,373,421 B2 | Page 1 of 1 |
| APPLICATION NO. | : 12/761445 | |
| DATED | : February 12, 2013 | |
| INVENTOR(S) | : Stefan Lindegger et al. | |

It is certified that error appears in the above-identified patent and that said Letters Patent is hereby corrected as shown below:

Title Page: Item (75)

Inventor last name "Muri" should read --Mueri--.

Signed and Sealed this
Twenty-third Day of September, 2014

Michelle K. Lee
*Deputy Director of the United States Patent and Trademark Office*